(12) United States Patent
Durand-Allen et al.

(10) Patent No.: US 8,545,504 B2
(45) Date of Patent: Oct. 1, 2013

(54) METHOD AND INSTRUMENTS FOR POSITIONING HUMERAL COMPONENT DURING SHOULDER ARTHROPLASTY

(75) Inventors: Anitra Durand-Allen, Warsaw, IN (US); Roy C. Wiley, Warsaw, IN (US); Louis Bigliani, Englewood, NJ (US); Evan Flatow, New York, NY (US); Ian Kelly, Glasgow (GB); George McCluskey, Columbus, GA (US); Anthony Miniaci, Cleveland, OH (US); Gregory Nicholson, Western Springs, IL (US); Michael Pearl, Los Angeles, CA (US); Ken Yamaguchi, Chesterfield, MO (US)

(73) Assignee: Zimmer, Inc., Warsaw, IN (US)

( * ) Notice: Subject to any disclaimer, the term of this patent is extended or adjusted under 35 U.S.C. 154(b) by 367 days.

(21) Appl. No.: 12/690,671

(22) Filed: Jan. 20, 2010

(65) Prior Publication Data

US 2010/0137925 A1 Jun. 3, 2010

Related U.S. Application Data

(62) Division of application No. 10/740,154, filed on Dec. 18, 2003, now Pat. No. 7,699,853.

(51) Int. Cl.
*A61F 2/46* (2006.01)
(52) U.S. Cl.
USPC .................. 606/86 R; 623/19.11; 606/99
(58) Field of Classification Search
USPC ............... 606/86 R–90, 99, 102, 100; 623/19.11–19.14, 22.11–22.2
See application file for complete search history.

(56) References Cited

U.S. PATENT DOCUMENTS

| 1,838,575 | A | 12/1931 | Schirmann |
| 2,185,723 | A | 1/1940 | Buckner |
| 2,543,780 | A | 3/1951 | Hipps et al. |
| D190,752 | S | 6/1961 | Pederson |
| 3,021,138 | A | 2/1962 | Smith |
| 3,590,814 | A | 7/1971 | Bennett et al. |

(Continued)

FOREIGN PATENT DOCUMENTS

CA 2483116 1/2011

OTHER PUBLICATIONS

"U.S. Appl. No. 10/740,154, Examiner Interview Summary mailed Feb. 10, 2009", 4 pgs.

(Continued)

*Primary Examiner* — Nicholas Woodall
*Assistant Examiner* — Melissa A Hall
(74) *Attorney, Agent, or Firm* — Schwegman, Lundberg & Woessner P.A.

(57) ABSTRACT

The present invention relates to a set of tools and accessories used for properly positioning a stemmed humeral component, and/or a humeral stem provisional, within a canal in the humerus. The set of tools and accessories includes one or more fin clamps that are configured to be temporarily attached to a fin on the humeral component or the provisional; a ruler that is configured to be attached to the arm of the fin clamp, a fixation pin and pin driver configured to be used with the other tools for marking a position on the humerus; and one or more sleeves that are configured to slide over the stem of the humeral stem provisional to maintain it in the desired position.

12 Claims, 7 Drawing Sheets

(56) References Cited

U.S. PATENT DOCUMENTS

| | | | |
|---|---|---|---|
| 3,857,389 | A | 12/1974 | Amstutz |
| D249,705 | S | 9/1978 | London |
| 4,378,607 | A | 4/1983 | Wadsworth |
| 4,642,121 | A | 2/1987 | Keller |
| 4,986,833 | A | 1/1991 | Worland |
| 4,993,410 | A | 2/1991 | Kimsey |
| 5,030,219 | A | 7/1991 | Matsen et al. |
| 5,058,465 | A | 10/1991 | Womack |
| 5,138,917 | A | 8/1992 | Kirschner |
| 5,236,460 | A | 8/1993 | Barber |
| 5,282,865 | A | 2/1994 | Dong |
| 5,462,563 | A | 10/1995 | Shearer et al. |
| 5,520,695 | A | 5/1996 | Luckman |
| 5,743,910 | A | 4/1998 | Bays et al. |
| 5,766,262 | A * | 6/1998 | Mikhail .................. 623/23.25 |
| 6,083,522 | A | 7/2000 | Chu et al. |
| 6,277,123 | B1 * | 8/2001 | Maroney et al. ............. 606/102 |
| 6,379,386 | B1 | 4/2002 | Resch et al. |
| 6,395,031 | B1 | 5/2002 | Foley et al. |
| 6,428,578 | B2 | 8/2002 | White |
| 6,503,255 | B1 | 1/2003 | Albrektsson et al. |
| 6,558,425 | B2 | 5/2003 | Rockwood, Jr. |
| 6,589,282 | B2 | 7/2003 | Pearl |
| 6,702,824 | B2 | 3/2004 | Maroney et al. |
| 6,712,823 | B2 | 3/2004 | Grusin et al. |
| 6,821,300 | B2 * | 11/2004 | Masini .................. 623/23.2 |
| 2001/0049561 | A1 | 12/2001 | Dews et al. |
| 2002/0095217 | A1 * | 7/2002 | Masini .................. 623/22.12 |
| 2003/0171816 | A1 * | 9/2003 | Scifert et al. ............... 623/22.12 |

OTHER PUBLICATIONS

"U.S. Appl. No. 10/740,154, Examiner Interview Summary mailed Nov. 2, 2009", 4 pgs.

"U.S. Appl. No. 10/740,154, Examiner Interview Summary mailed Nov. 28, 2007", 3 pgs.

\* cited by examiner

METHOD AND INSTRUMENTS FOR POSITIONING HUMERAL COMPONENT DURING SHOULDER ARTHROPLASTY

CROSS-REFERENCE TO RELATED APPLICATIONS

This is a Divisional of U.S. patent application Ser. No. 10/740,154 filed Dec. 18, 2003, entitled METHOD AND INSTRUMENTS FOR POSITIONING HUMERAL COMPONENT DURING SHOULD ARTHROPLASTY, the disclosure of which is expressly incorporated herein by reference.

The present invention relates generally to obtaining the proper position of a prosthetic implant, and more specifically to devices and methods used for achieving the proper axial position and retroversion of a stemmed humeral component during shoulder arthroplasty, as well as to properly positioning a humeral stem provisional, which is inserted on a trial basis during the operation, prior to inserting the permanent stemmed humeral component.

BACKGROUND OF THE INVENTION

Shoulder fractures are not uncommon, especially among senior citizens with osteoporosis. In certain instances, shoulder replacement surgery is necessary. One type of fracture that commonly requires shoulder replacement surgery is called a four-part fracture. Such a fracture is characterized by the shoulder being broken into four parts—the lesser tuberosity, the greater tuberosity, the humeral head, and the humeral shaft.

During a shoulder replacement operation (also known as shoulder arthroplasty surgery), a canal found within the humeral shaft is used for receiving the humeral component of the shoulder prosthesis. If necessary, in order to better accommodate the humeral component, the canal may be enlarged using known methods. The humeral component of the prosthesis typically includes a stem and a head, which is a partial sphere that replaces the fractured humeral head. The stem and the head may be two separate components, or they may be a single component. Regardless of whether the humeral component is a single part or two parts, a collar is formed between the stem and the head. Between this collar and the fracture line on the proximal end of the humerus, the fractured lesser and greater tuberosities are normally anchored around the stem of the humeral component, as closely as possible to their original positions.

Before implanting the permanent stemmed humeral component, a temporary component, often called a humeral stem provisional, is temporarily inserted into the humerus to determine the proper placement of the stemmed humeral component. Proper positioning of the final stemmed humeral component is very important. Improper positioning can result in a range of problems from mild discomfort to severe pain, as well as a lack of proper range of motion, depending upon the degree and type of improper positioning. Accordingly, it is important that the humeral stem provisional be properly positioned, and that such proper position can be reliably replicated when implanting the final stemmed humeral component. The two key areas of proper positioning are the stemmed component's axial position and its retroversion.

Currently, several devices are available to assist in properly positioning the stemmed humeral component within the humerus. For example, Tornier® markets a system under the Aequalis® name that includes a jig that uses a portion of the anatomy for referencing the position of the humeral implant. However, this jig is relatively large and bulky, and it is difficult to perform a range of motion analysis with the jig in place. Other smaller systems, such as the DePuy® Global™ Fx System also include a positioning jig. Although the jig of the Global™ Fx System allows for better range of motion analysis than the Tornier® system, the Global™ Fx System still includes a somewhat large positioning jig, which could benefit from being changed to a more low profile system. Thus, an improved system for properly positioning the stemmed humeral component is desired.

BRIEF SUMMARY OF THE INVENTION

The present invention relates to a set of tools and accessories used for properly positioning a stemmed humeral component, and/or a humeral stem provisional, within a canal in the humerus. The set of tools and accessories includes one or more fin clamps that are configured to be temporarily attached to a fin on the humeral component or the provisional; a ruler that is configured to be attached to the arm of the fin clamp, a fixation pin and pin driver configured to be used with the other tools for marking a position on the humerus; and one or more sleeves that are configured to slide over the stem of the humeral stem provisional to maintain it in the desired position.

More specifically, the present invention includes a fin clamp for positioning a stemmed humeral component, or a humeral stem provisional, within a humerus during shoulder arthroplasty, where the fin clamp includes a head and an arm connected to the head. The head is configured to be seated between a proximal end of the humerus and a distal side of a collar of the stemmed humeral component or the humeral stem provisional, such that the head separates the proximal end of the humerus from the distal side of the collar by a predetermined distance. Preferably, the head includes an attachment arrangement to attach the fin clamp to a fin that extends radially outwardly from the stem of the humeral component or the provisional.

The present invention also includes a system of fin clamps for positioning a stemmed humeral component, or a humeral stem provisional, within a humerus during shoulder arthroplasty, where the system of fin clamps includes a plurality of fin clamps. The system of fin clamps preferably includes at least two fin clamps, and more preferably includes three fin clamps. The first one of the plurality of fin clamps is configured and arranged to separate the proximal end of the right humerus from the distal side of the collar by a first predetermined distance and to separate the proximal end of the left humerus from the distal side of the collar by a second predetermined distance. The second one of the plurality of fin clamps is configured and arranged to separate the proximal end of the right humerus from the distal side of the collar by the second predetermined distance and to separate the proximal end of the left humerus from the distal side of the collar by the first predetermined distance, where the first predetermined distance is different from the second predetermined distance. The third one of the plurality of fin clamps is configured and arranged to separate the proximal end of either the right humerus or the left humerus from the distal side of the collar by a third predetermined distance, where the third predetermined distance is different from both the first predetermined distance and the second predetermined distance.

The present invention also relates to a method for positioning a stemmed humeral component within a humerus during shoulder arthroplasty. The method includes the steps of inserting the stemmed humeral component, with a fin clamp attached, into a canal located in the humerus at an estimated position and seating the humeral component at an intended position by making contact between the distal side of the fin clamp and the proximal end of the humerus, whereby the collar of the humeral component is seated at a certain predetermined distance from the proximal end of the humerus. If desired, the fin clamp may be attached to the stemmed humeral component after the component has been inserted into the humeral canal, instead of attaching it prior to insertion into the humeral canal. Preferably, the inserting step and the seating step are each performed twice, once for a humeral stem provisional and once for the stemmed humeral component. Optionally, the method may include a step of attaching a sleeve upon the stem of the humeral stem provisional prior to the inserting step, where the sleeve helps to secure the humeral stem provisional in position within the humeral canal.

In addition, the present invention also relates to a method for temporarily securing a humeral stem provisional within a humerus during shoulder arthroplasty. The method includes the steps of attaching a sleeve to a stem of the humeral stem provisional and inserting the humeral stem provisional, with the sleeve attached thereto, into a canal located within a proximal portion of the humerus. After determining that the humeral stem provisional is properly sized and positioned, the humeral stem provisional and the sleeve are removed, and a permanent humeral component is implanted in the same location and orientation as the humeral stem provisional previously removed. In order to mark and recreate the position of the provisional when implanting the permanent humeral component, a ruler and a fixation pin may be used.

Also included as part of the present invention is a system of humeral stem provisionals and at least one sleeve, which are intended to be used during shoulder arthroplasty. The system includes a plurality of humeral stem provisionals each including a stem and at least one sleeve configured to fit upon the stem of each humeral stem provisional. The sleeve aids in securely seating the associated humeral stem provisional within a canal located within a proximal portion of a humerus.

The present invention also relates to a ruler for use in positioning a stemmed humeral component, or a humeral stem provisional, within a humerus during shoulder arthroplasty. The ruler preferably includes a scale with incremental marks indicting distance from a zero point; and a securing assembly for securing the ruler to another device used for positioning a stemmed humeral component, or a humeral stem provisional, within a humerus during shoulder arthroplasty.

Finally, the present invention also relates to a system that includes a fixation pin and a driver used for inserting the fixation pin into a bone for marking the orientation of a provisional prosthesis in order to duplicate proper orientation for the final prosthesis. The system preferably includes a fixation pin with a threaded portion near a first end and a portion of non-circular cross-section near a second end thereof; and a driver that includes a first end portion and a second end portion. The first end portion preferably includes an axially extending aperture with a portion thereof that is of a non-circular cross-section that corresponds to the non-circular cross-section of the fixation pin. The second end portion of the driver is preferably configured to either accept a T-handle (for manual rotation) or to be attached to a drill (for mechanized rotation).

BRIEF DESCRIPTION OF THE DRAWINGS

Preferred embodiments of the present invention are described herein with reference to the drawings wherein.

DETAILED DESCRIPTION OF THE INVENTION

The present invention relates to a system of components used for properly positioning the stemmed humeral component of a shoulder prosthesis, and/or to positioning the humeral stemmed provisional, as well as to the methods of using those positioning components. The system includes one or more fin clamps, version pins, a specially configured ruler, one or more sleeves designed to be attached to the humeral stemmed provisional, a fixation pin and a driver for the fixation pin.

Figure 1:
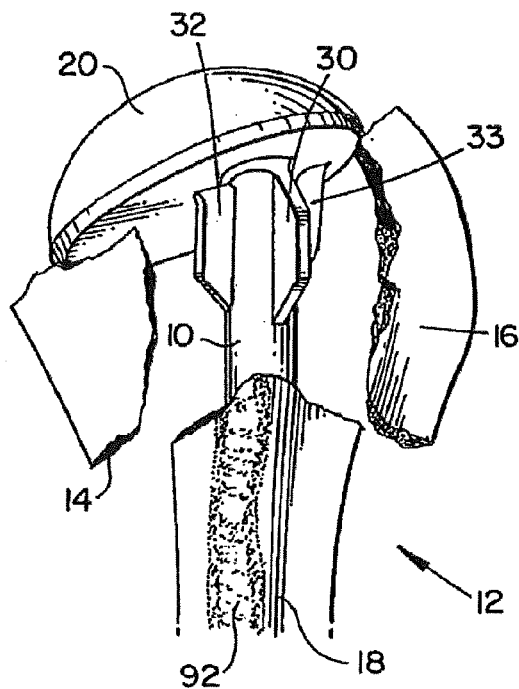
FIG. 1 is a view of a fractured humerus, with a stemmed humeral component and head inserted into a canal within the humerus.

FIG. 1 shows one example of a stemmed humeral component 10 inserted within a humerus that has suffered a classic four-part fracture. In a four part fracture, bone has fractured into the following four parts—the lesser tuberosity 14, the greater tuberosity 16, the humeral shaft 18, and the humeral head (not shown). During shoulder arthroplasty, the stemmed humeral component 10, including a humeral head 20 (which may be a separate component or may be integrally formed with the humeral component), is implanted into a canal that is naturally found in the humeral shaft 18 (if necessary, the humeral canal may be enlarged), and the lesser and greater tuberosities (14 and 16) are refitted and secured around the stemmed humeral component 10 in locations as close as possible to their original anatomical positions. It should be noted that although the present specification shows and describes only one example of a type of stemmed humeral component and provisional, it is contemplated that the present invention could also be applied to stemmed humeral components and provisionals of many different configurations.

In order for the shoulder prosthesis to mimic the original range of motion of the shoulder joint, it is very important for all of the components of the prosthesis to be properly positioned. The present invention relates to positioning the stemmed humeral component, as well as to positioning a humeral stem provisional, the stem of which is configured to match the permanent stemmed humeral component. As known in the art, the humeral stem provisional is temporarily placed in position in the humeral canal prior to permanently positioning the permanent stemmed humeral component.

Figure 2:
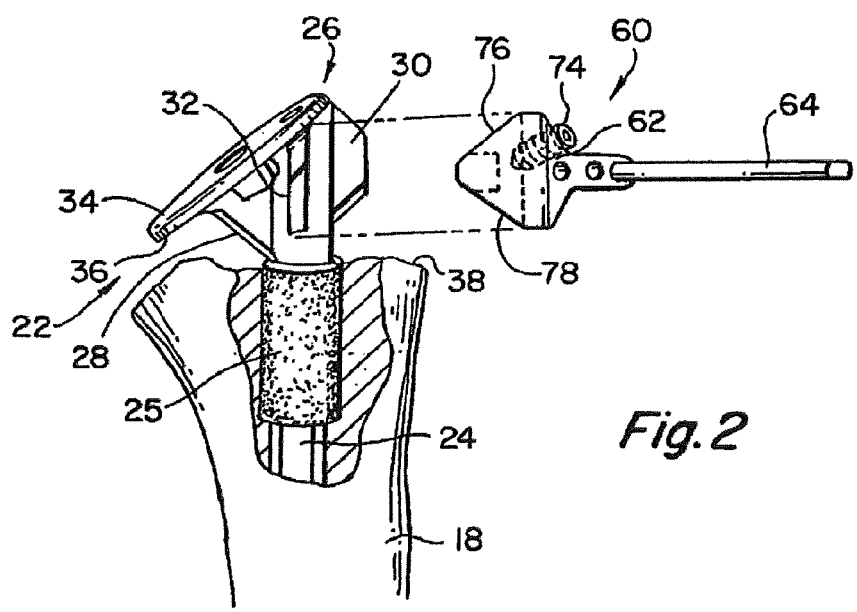
FIG. 2 is a view showing the fin clamp and a sleeve for positioning a humeral stem provisional within a canal in the humerus.

Turning now to FIG. 2, one example of a humeral stem provisional 22 is shown inserted into a canal within a left humeral shaft 18. Since the provisional itself and the process of enlarging the humeral canal (if necessary) are not part of this invention, and also since different types of provisionals and several prior art methods of enlarging the humeral canal are known, these aspects will not be discussed in detail, except as necessary for understanding the present invention. Further, for ease of description, the implants, tools and procedures shown and described will normally only be described for use with the left shoulder. However, one of ordinary skill in the art can easily apply and modify, where necessary, the implants, tools and procedures for use with the right shoulder. As can be seen in FIG. 2, the humeral stem provisional 22 in this example includes a stem 24, a collar 26, and four fins that extend radially outwardly of the stem—a medial fin 28, a lateral fin 30, an anterior fin 32, and a posterior fin 33 (shown in FIG. 1) that is a mirror image of the anterior fin 32. The collar 26 of the provisional 22 has a proximal side 34 and a distal side 36.

Seated upon the stem 24 is a sleeve 25, which is preferably made of foam or other compressible material. The sleeve 25 serves to maintain the humeral stem provisional 22 in position during intraoperative assessment of its axial height and version. In other words, because the stem provisional 22 is not cemented or otherwise rigidly held in place, it may move from the intended position. However, by attaching the sleeve 25 to the stem 24 prior to insertion of both into the canal located within the humeral shaft 18, the position of the provisional 22 is maintained. Although the sleeve 25 helps to maintain the provisional 22 in position, the addition of the sleeve 25 to the stem 24 of the provisional 22 does not create such a tight fit that the provisional cannot be moved at all. Thus, even with the sleeve 25 in place, the position of the provisional 22 can be adjusted, if necessary. However, the sleeve 25 provides a tight enough fit within the humeral canal to prevent unintended movement of the provisional 22 within the canal.

Figure 3:
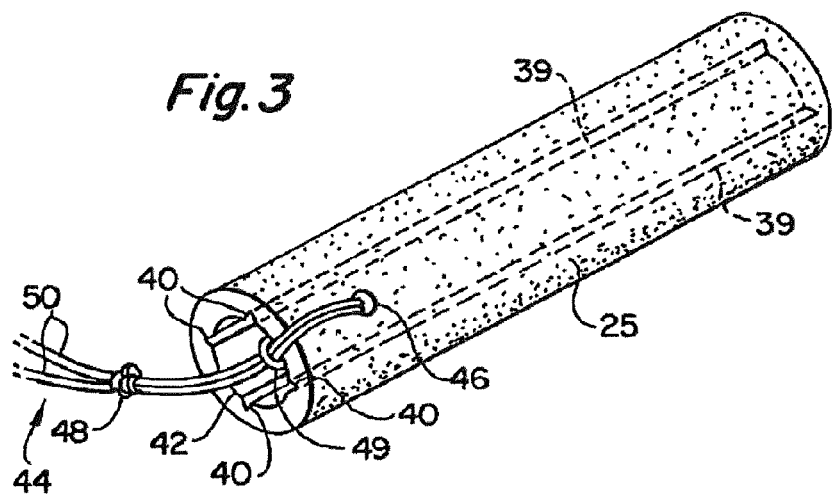
FIG. 3 is a perspective view of a sleeve that is intended to be used to maintain the position of a humeral stem provisional within the humeral canal.

Turning now to FIG. 3, a perspective view of a preferred embodiment of the sleeve 25 is shown. Basically, the sleeve 25 is cylindrical in shape, and is preferably made of foam or other similar material. Preferably, the sleeve 25 is manufactured by stamping multiple hollow cylindrical-shaped sleeves from a flat sheet of foam (i.e., by axially stamping the sleeves). Alternatively, the sleeve 25 may be manufactured by rolling a flat, rectangular piece of foam into the hollow cylindrical shape shown, with the rolled edges being glued or otherwise affixed together along an axial line 39. Other methods of fabrication are also contemplated, such as injection molding, in which case the cylindrical shape can be directly formed. In order to provide better gripping upon the stem, as well as to make the sleeve suitable for use with stems of different diameters, four slits 40 are provided to run axially along the sleeve's inner periphery 42. The slits 40 are preferably between 1 mm and 2 mm in depth, although other depths are also contemplated. Although four slits are shown in this example, a different number of slits may also be used, or the slits may be omitted entirely, if desired.

The sleeve 25 also preferably includes a tether 44 that is attached via a hole 46 formed within a sidewall of the sleeve 25. In most cases, the to tether will not be used because the sleeve 25 will remain attached to the stem 24 of the provisional 22 when the provisional is removed from the humeral canal. However, if the sleeve somehow slips off of the provisional 22, the tether 44 may be used to pull the sleeve 25 out of the humeral canal. Thus, the tether should be long enough to extend out of the humeral canal, with sufficient length for gripping. For example, in the preferred embodiment, the tether extends from the hole 46 about eight inches. Of course, the length of the tether may be varied to be longer or shorter, if desired.

The tether 44 is preferably made of suture or other strong thread, and is preferably a looped thread that has a knot 48 near the looped end 49. To secure the tether 44 to the sleeve 25, the looped end 49 is passed through the hole 46 until it extends out through the end of the sleeve 25. Then the free end 50 and the knot 48 are passed through the looped end 49, and the free end is pulled to tighten the tether. Of course, other methods of attaching the tether to the sleeve are also contemplated.

Preferably, the sleeve 25 will be available in a variety of sizes because there are a variety of sizes of humeral stem provisionals. Thus, for example, there may be a different sized sleeve for each different size of humeral stem provisional. However, in order to reduce the number of different sizes of sleeves that need to be stocked, each sleeve can preferably be configured to be used with several differently sized provisionals. For example, if humeral stem provisionals are available in thirteen different sizes, only four different sizes of sleeves are preferably needed, with each sleeve being able to fit three or four differently sized provisionals. The following chart provides a helpful example of how the sleeves can be sized:

| EXTERIOR DIAMETER OF SLEEVE | INTERIOR DIAMETER OF SLEEVE | INTERIOR DIAMETER OF SLEEVE (INCLUDING TWO SLITS) | STEM DIAMETER OF PROVISIONAL |
| --- | --- | --- | --- |
| 12 mm | 6 mm | 8 mm | 6 mm-8 mm |
| 16 mm | 9 mm | 11 mm | 9 mm-11 mm |
| 20 mm | 12 mm | 15 mm | 12 mm-14 mm |
| 24 mm | 16 mm | 20 mm | 15 mm-18 mm |

As indicated in the chart above, for thirteen different provisional sizes with stem diameters between 6 mm and 18 mm (in 1 mm increments), only four different sleeves are needed because a 6 mm interior diameter sleeve fits provisionals with stems of diameters between 6 mm and 8 mm; a 9 mm interior diameter sleeve fits stems between 9 mm and 11 mm; a 12 mm interior diameter sleeve fits stems between 12 mm and 14 mm, and a 16 mm sleeve fits stems between 15 and 18 mm. One reason that the sleeves can be used with provisionals of different sizes is that the four slits 40 allow the inner diameter of the sleeves to slightly adjust to accommodate the different diameter stems of provisionals of different sizes. As shown in the chart, a sleeve with a 12 mm exterior diameter has an interior diameter of 6 mm (in the area without any slits), but it has an interior diameter of 8 mm in the area with two of the slits because each slit is 1 mm in depth (thereby the diameter is increased by 2 mm because the two slits face each other). Likewise, the slits in the 16 mm exterior diameter sleeve are also each preferably 1 mm in depth. The slits in the 20 mm exterior diameter sleeve are each preferably 1.5 mm in depth, and the slits in the 24 mm exterior diameter shaft are each preferably 2 mm in depth. Additionally, the axial length of all of the sleeves can be the same. For example, the axial length of each sleeve is preferably between 20 and 40 mm. Of course, the dimensions mentioned above, and in other parts of this specification, are only examples of suitable dimensions, and other appropriate dimensions can be determined by those of ordinary skill in the art.

For ease of identification to distinguish the differently sized sleeves from one another, each of the sizes can be made of a different color, if desired. Accordingly, since there are four different sizes of sleeves in the example above, four different colors of foam would be used to produce the sleeves. However, since the most likely instances of confusion arise between sleeves that are only slightly larger or slightly smaller than each other, it may only be necessary to use two different colors, alternating between the two colors as the sleeves increase in size. For example for a set of four sleeves of exterior diameters of 12 mm, 16 mm, 20 mm and 24 mm, the 12 mm and 20 mm sleeves could be of a first color, and the 16 mm and 24 mm sleeves could be of a second color that is different from the first color. Such a system works because it is unlikely that someone would be confused between the 12 and 20 mm sleeves or between the 16 and 24 mm sleeves. By only using two colors instead of four, manufacturing costs are reduced.

Figure 7:
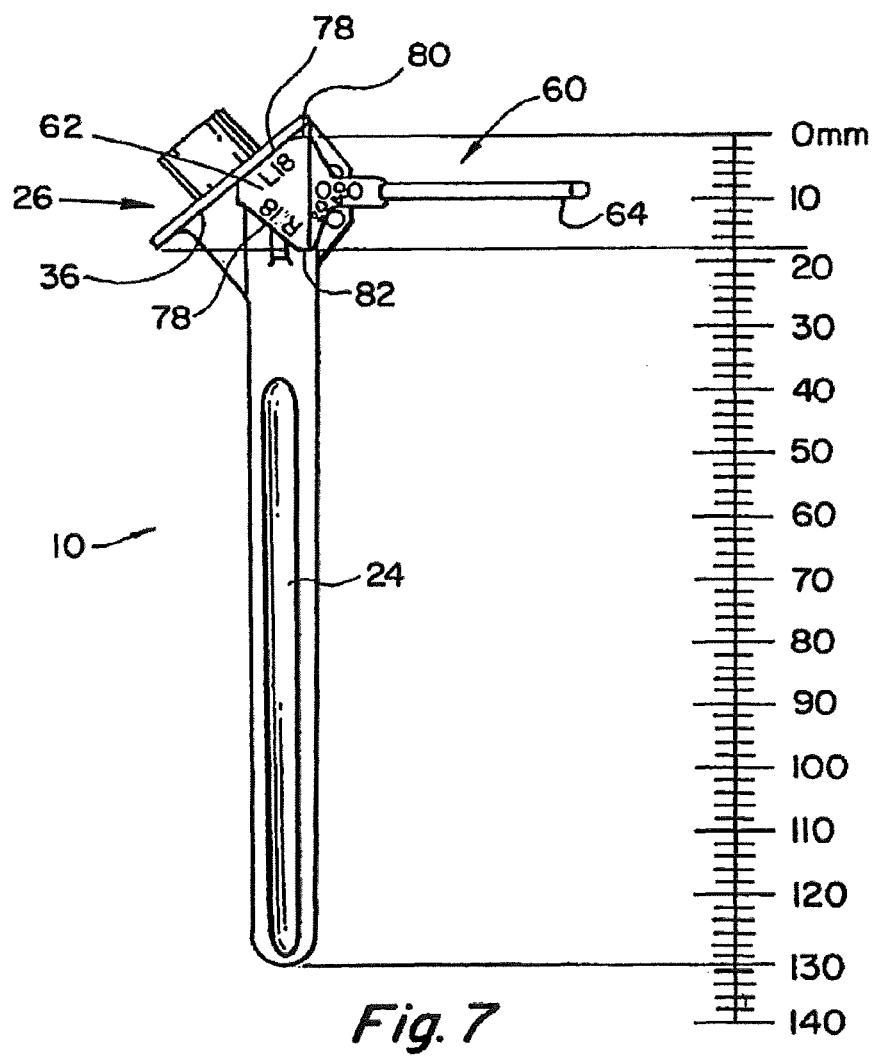
FIG. 7 is a front view of the fin clamp of FIG. 4 attached to a humeral stem provisional, and including a scale to show the zero point.

Turning back to FIG. 2, another important aspect of the present invention will be described—fin clamp 60. Fin clamp 60 is preferably made of stainless-steel or other metal, but other materials, such as plastic, may also be used. As described more fully below, the fin clamp 60 is used to properly position the stemmed humeral component (and the humeral stem provisional) with regard to both its axial height and its retroversion. Axial height positioning will be discussed first. FIG. 7 shows one example of a fin clamp 60 attached to a stemmed humeral component 10, which is shown alongside a measurement scale. In the preferred embodiment, the zero point of the scale is taken as the point where the center axis of the stem 24 meets the distal side 36 of the collar 26. This zero point, and the rest of the numbering scale, is the same one currently used on other tools and templates in the Bigliani/Flatow® Shoulder Arthroplasty System, manufactured by Zimmer Inc. of Warsaw, Ind. However, it is not necessary to use the same scale as the Bigliani/Flatow® System, and other measurement systems and/or zero points may be used instead of those described.

Analysis has shown that in most fracture situations, the distal side 36 of the provisional's collar 26 should be spaced a certain distance from the proximal surface 38 of the humeral shaft 18. (Of course, since the relevant portions of the provisional are sized and shaped identically to those of the permanent stemmed humeral component, the collar of the permanent component, as well as the other portions of the permanent component, should be positioned identically to those of the provisional.) More specifically, in most average sized adults, it has been found that in four-part fracture scenarios, the fractured joint is best rebuilt by positioning the stemmed humeral component so that there is 18 mm of space separating the distal side 34 of the collar 26 (at the anterior fin) from the proximal surface 38 of the humeral shaft 18. However, in certain cases, the appropriate spacing is either slightly less or slightly greater than 18 mm. For example, certain situations require a 15 mm space and other cases require 21 mm of space. Accordingly, as described below, the preferred embodiment of the invention includes a set of fin clamps that are configured to provide spacing of the following predetermined distances: 15 mm, 18 mm, and 21 mm, in order to obtain the proper spacing in a variety of different situations. However, the invention is not limited to these sizes.

First, fin clamp 60, which provides 18 mm spacing, will be described. The fin clamp 60 is configured to be attached to the anterior fin 32 of the humeral stem provisional 22, as shown in the exploded view of FIG. 2. Likewise, because the stemmed humeral component 10 has essentially the same configuration as the provisional 22, the fin clamp 60 is also configured to be attached to the anterior fin of the stemmed humeral component in the same manner as attached to the provisional.

As shown in FIGS. 2, 4, 5 and 6, the fin clamp 60 includes a head 62 and an arm 64. The head 62 is configured to be seated upon the anterior fin 32 so that the head 62 is positioned between the proximal end surface 38 of the humerus 18 and the distal side 36 of the collar 26. In this embodiment, the head 62 separates the proximal end surface 38 of the humerus from the distal side 36 of the collar 26 by 18 mm. This embodiment of the fin clamp 60 is called the "universal" fin clamp because it can be used in most situations and because it can be used on either the left humerus (as shown in FIG. 2) or on the right humerus, with the separation distance for each side being the same (18 mm). Other embodiments of the fin clamp, which will be described below, are also configured to be used on either the left humerus or the right humerus, but in these other embodiments, the separation distances are not the same for both sides.

The head 62 includes a channel 66 (best seen in FIG. 6) that is configured to accept the anterior fin 32 of both the humeral stem provisional 22 and the stemmed humeral component 10. Preferably, the channel 66 is just slightly deeper than the radial length of the anterior fin 32, and is defined from side-to-side between an endblock 67 and a wall 69. An attachment arrangement that includes one or more setscrews is provided in order to attach the fin clamp 60 to the anterior fin 32. More specifically, the preferred embodiment includes two threaded holes 68, 70 (best shown in FIG. 5) that extend through the wall 69, and two setscrews 72, 74, with one setscrew being seated in each threaded hole. If desired, only one setscrew may be provided for both holes, in which case the user simply inserts the single setscrew into the appropriate hole. Preferably, the setscrews include sharp pointed tips for providing more secure attachment to the fin.

In order to attach the fin clamp 60 to the anterior fin 32, one of the setscrews (72 or 74) is tightened so that it extends through the wall 69 and makes contact with fin 32. Preferably, whichever setscrew is positioned on the proximal side will be tightened because easier access is provided for that one. Thus, if the fin clamp 60 is being used during left shoulder arthroplasty, setscrew 74 is the proximal setscrew and it will be tightened, and if it is being used during right shoulder arthroplasty, setscrew 72 is the proximal one, and it will be tightened.

Figure 4:
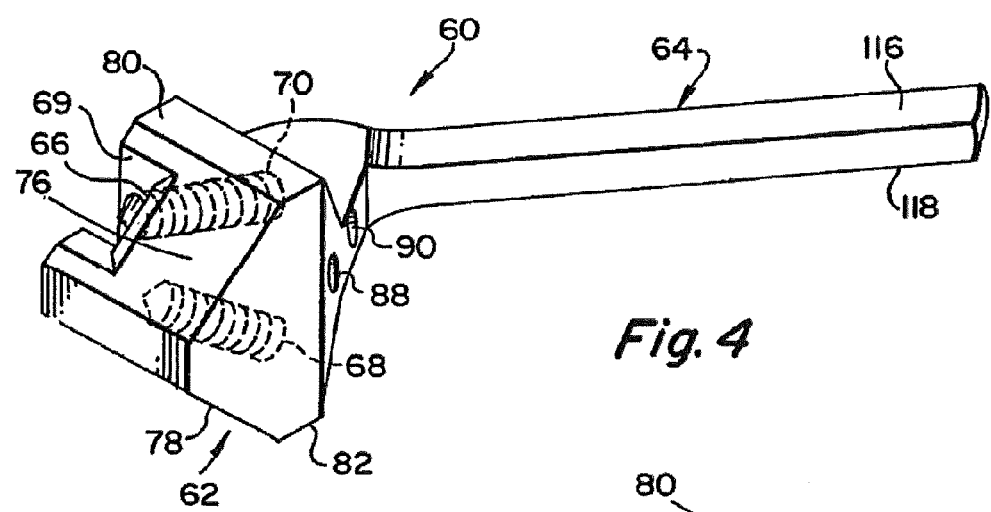
FIG. 4 is a perspective view of one type of fin clamp, shown from the top and front side.
Figure 5:
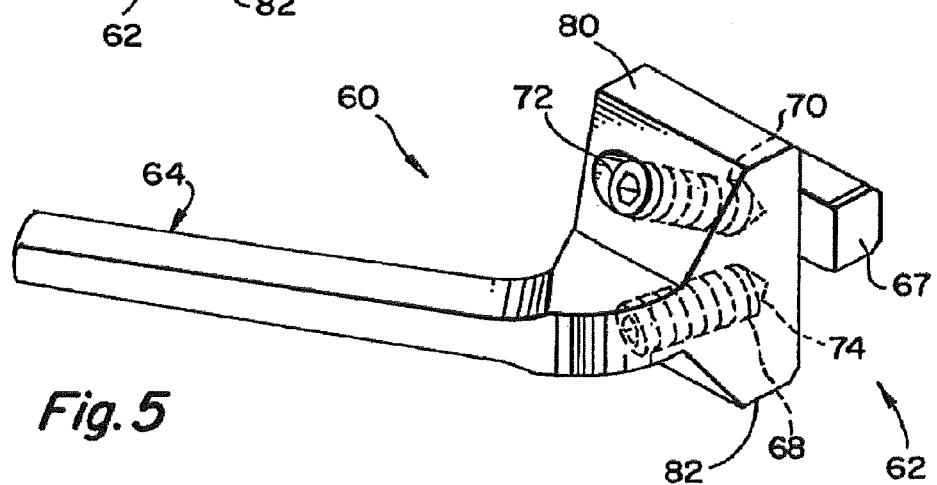
FIG. 5 is a different perspective view of the fin clamp of FIG. 4, shown from the bottom and rear side.

The fin clamp's head 62 includes two angled surfaces 76 and 78, as most clearly shown in FIGS. 2 and 4, which are symmetric to each other and which correspond to the angle of the distal side 36 of the collar 26 of the humeral stem provisional 22 and the stemmed humeral component 10 (shown in FIG. 7). Flat surfaces 80 and 82 are also included adjacent to the angled surfaces 76 and 78, respectively. These surfaces are configured in this manner so that the surgeon can easily tell that the fin clamp 60 is properly positioned (and therefore the provisional 22 or the humeral component 10 is also properly positioned) by noting when one of the angled surfaces (76 or 78) contacts the distal side 36 of the collar 26 and the opposite flat surface (either 82 or 80) contacts the proximal surface 38 of the humeral shaft. More specifically, during left shoulder arthroplasty, proper axial positioning has been obtained when angled surface 78 contacts the distal side 36 of the collar 26 and the flat surface 82 contacts the proximal surface 38 of the humeral shaft. If the universal fin clamp 60 is positioned in this manner, the desired 18 mm separation is provided. For ease of description, the invention is being described and shown as applied to a left humeral stem provisional only (as well as to a left stemmed humeral component only). However, the universal fin clamp 60 can also be used with a right provisional or right humeral component if the fin clamp is flipped so that the opposite angled surface is the one making contact with the collar of the provisional (or humeral component).

In order to facilitate obtaining the proper orientation of the fin clamp 60, markings indicating the proper orientation of the fin clamp are preferably provided. Different markings need to indicate the proper orientation for use during left shoulder arthroplasty and during right shoulder arthroplasty, because the orientation of the fin clamp is not the same for each side. One example of such markings is shown in FIG. 7, which includes the markings L18 and R18. These markings indicate that this fin clamp provides 18 mm separation distance, and they also show the proper orientations of the fin clamp when used on either the left shoulder or the right shoulder. More specifically, in this example, when the fin clamp is used during an operation on the left shoulder, the designation L18 is upright (as shown in FIG. 7), and when used during an operation on the right shoulder, the designation R18 is upright. Of course, other types of markings may also be used, or the markings may be omitted entirely, if desired.

Figure 14:
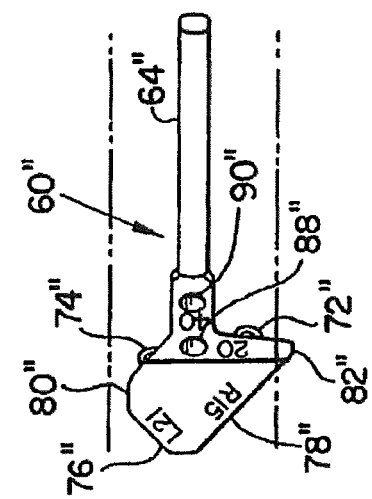
FIG. 14 is a front view of the fin clamp of the earlier figures, which creates the same predetermined distance whether used for the right humerus or the left humerus.
Figure 15:
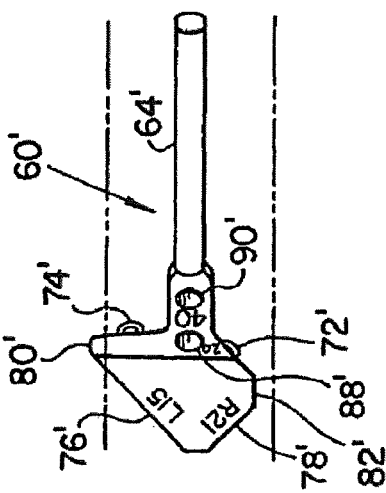
FIG. 15 is a front view of a second fin clamp, which creates different predetermined distances for the right humerus and the left humerus.
Figure 16:
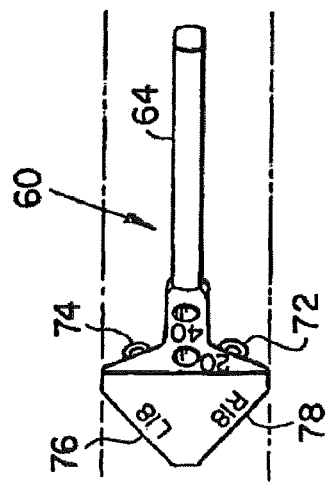
FIG. 16 is a front view of a third fin clamp, which creates different predetermined distances for the right humerus and the left humerus that are reversed from those of the in clamp shown in FIG. 15.

Turning now to FIGS. 15 and 16, two additional embodiments of the fin clamp will be described. The fin clamps of FIGS. 15 and 16 are used for creating predetermined separation distances other than the 18 mm distance described above with regard to fin clamp 60. FIG. 15 shows fin clamp 60' and FIG. 16 shows fin clamp 60". FIG. 14, which shows the first embodiment, fin clamp 60, has been provided in order to easily compare the configurations of fin clamps 60' and 60" with that of fin clamp 60. Fin clamps 60' and 60" are essentially the same as fin clamp 60, except that they provide different separation distances than fin clamp 60. Additionally, fin clamps 60' and 60" are not symmetric about their respective central axis, as fin clamp 60 is.

More specifically, fin clamp 60' of FIG. 15 is configured to provide a separation distance of 15 mm when used during left shoulder arthroplasty, as designated by the marking "L15," and to provide a separation distance of 21 mm when used during right shoulder arthroplasty, as designated by the marking "R21" (which is nearly upside-down in FIG. 15). As with the universal fin clamp 60, which has designations L18 and R18, the surgeon can tell which direction the clamp should be oriented and the separation distance created by the clamp by looking at the designations L15 and R21. More specifically, with fin clamp 60', when this fin clamp is used during an operation on the left shoulder, the designation L15 should be upright (and a 15 mm separation will be provided), and when used during an operation on the right shoulder, the designation R21 should be upright (and a 21 mm separation will be provided).

Fin clamp 60" of FIG. 16 merely provides the opposite configuration to that of clamp 60' of FIG. 15. Thus, fin clamp 60" can provide a 21 mm separation distance during left shoulder arthroplasty, and it can provide a 15 mm separation during right shoulder arthroplasty. More specifically, with fin clamp 60", when this fin clamp is used during an operation on the left shoulder, the designation L21 should be upright (and a 21 mm separation will be provided), and when used during an operation on the right shoulder, the designation R15 should be upright (and a 15 mm separation will be provided).

In order to allow the surgeon to be able to accommodate situations where any one of the three different separation distances (15 mm, 18 mm and 21 mm) is to be provided, a system, or kit, that includes several different fin clamps should be provided. More specifically, in the preferred embodiment of the kit or system, three different fin clamps are provided—fin clamp 60, fin clamp 60' and fin clamp 60". Accordingly, with the kit, the most commonly desired separation distances can reliably be obtained.

Figure 8:
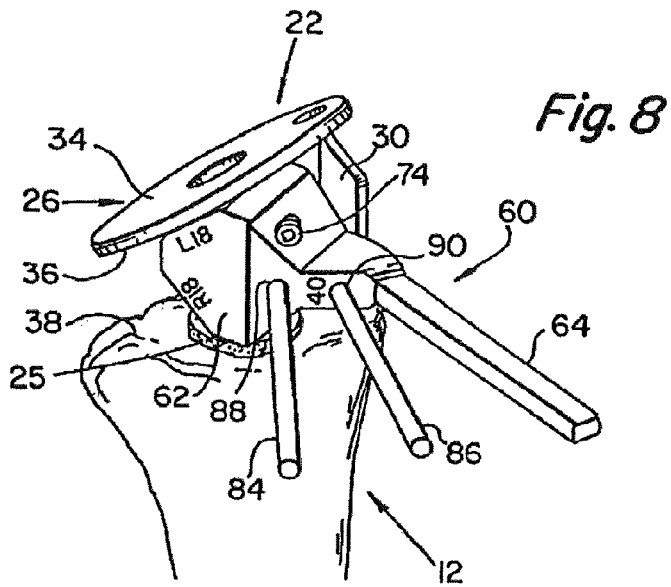
FIG. 8 is a view similar to FIG. 2, except this figure shows the two version pins used to test the range of motion.

As mentioned above, in addition to obtaining the correct axial spacing, the present invention also provides a way to set the proper retroversion of the humeral stem provisional and the stemmed humeral component. Turning now to FIG. 8, the humeral stem provisional 22 is shown seated within a canal in the left humerus 12, and the fin clamp 60 has been secured to the anterior fin by tightening the setscrew 74.

The first step for obtaining the proper retroversion of the provisional 22 and/or the humeral component 10 relates to aligning the arm 64 with respect to the approximate position of the bicipital groove in an intact humerus (FIG. 1 shows a bicipital groove 92), if clear evidence of the groove is still available. If the bicipital groove cannot be located, the surgeon may simply estimate its position, and align arm 64 with that estimation, or slightly posterior to the estimated position of the groove.

Figure 6:
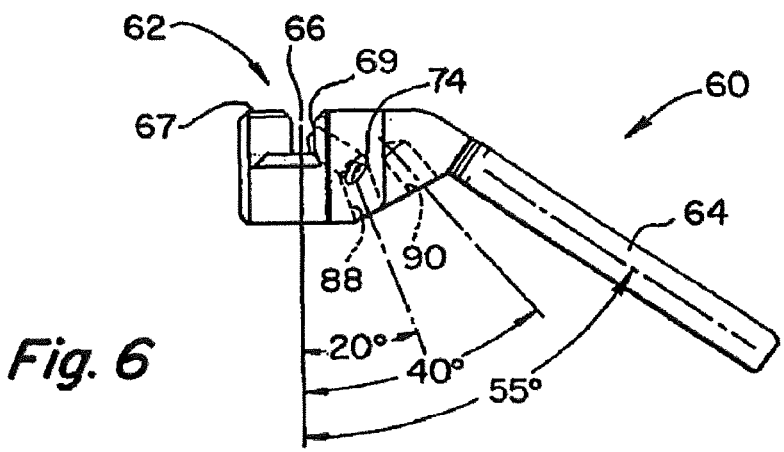
FIG. 6 is a top view of the fin clamp of FIG. 4.

FIG. 6 shows that the arm angle is preferably 55 degrees from the anterior fin 32 (and 55 degrees from the axial stem of the humeral component 10 and the provisional 22, when the fin clamp is attached thereto). Designing the arm 64 of the fin clamp 60 to be at the 55 degree angle to align with the bicipital groove has several advantages. The fracture line between the lesser tuberosity 14 and the greater tuberosity 16 typically occurs either in line with, or slightly posterior to, the bicipital groove 92, as shown in the FIG. 1 example. Because the 55 degree angle aligns the arm 64 of the fin clamp with this fracture line, the arm 64 does not interfere with the surgeon's task of reorienting the tuberosities to confirm the position of the provisional 22 and/or the humeral component 10 while the fin clamp is attached to the provisional or the humeral component. In addition, with the arm 64 of the fin clamp configured at this angle, the arm does not interfere with a range of motion analysis.

The second step for obtaining the proper retroversion involves the use of two version pins. In FIG. 8, two version pins 84 and 86 are shown inserted into two version pin holes 88, 90, respectively (the version pin holes are also shown in FIG. 4, without the version pins inserted therein). Turning now to FIG. 6, version pin hole 88 is set to be 20 degrees from channel 66 (which sets it at 20 degrees from the anterior fin 32 and 20 degrees from the axial stem of the humeral component 10 and the provisional 22, when the fin clamp is attached thereto). In a similar manner, version pin hole 90 is set to be 40 degrees from channel 66 (and 40 degrees from the anterior fin and the axial stem of the humeral component 10 and the provisional 22, when the fin clamp is attached thereto). When the two version pins 84 and 86 are seated within the appropriate version pin holes 88 and 90, as shown in FIG. 8, the retroversion of the provisional 22 or the humeral component 10 can be tested by extending the patient's arm to make sure that the patient's forearm is centered between the version pins 88 and 90. To avoid confusion regarding the use of version pin holes 88 and 90, it is desirable to have them marked with degree indications "20" and "40," as shown in FIG. 4. However, such markings are not required. It should be noted that the 20 and 40 degree orientations of the version pins and the 55 degree stem angle shown and described are intended to be used for guidance to obtain proper retroversion. In certain situations, proper retroversion, as discovered during a range of motion analysis, will differ from these guidelines.

Once the proper axial height and the version of the provisional 22 has been established, and the provisional is located in the desired position, it is useful to mark that position to facilitate the placement of the permanent stemmed humeral component 10 into the exact same position. The present invention includes the following tools for marking the position—a specially configured ruler that can be attached to the arm of the fin clamp and a fixation pin and pin driver for temporarily inserting the pin into the humerus at a desired location along the scale of the ruler.

Figure 9:
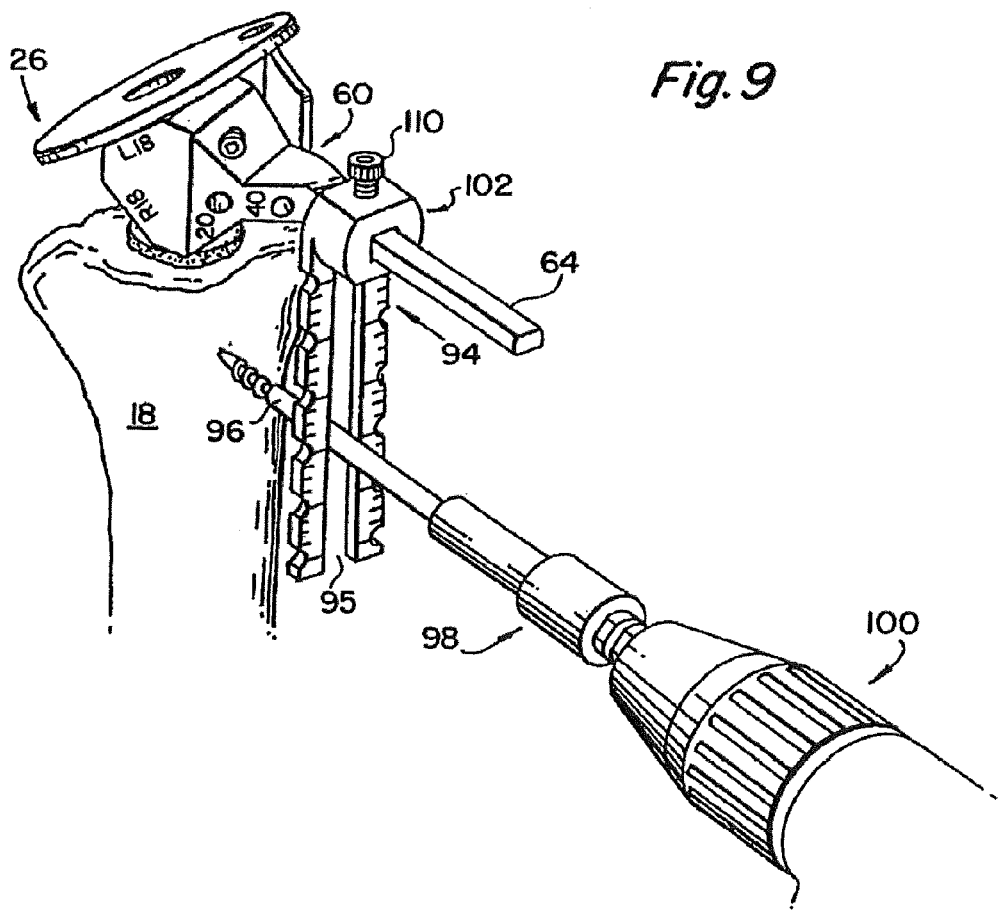
FIG. 9 is another view similar to FIG. 2, except this figure shows the ruler in place, and the driver being used to insert a fixation pin into the bone.

FIG. 9 shows one example of a specially configured ruler 94 attached to the arm 64 of fin clamp 60, with fixation pin 96 being inserted into a slot (or elongated hole) 95 in the ruler via a pin driver 98 that is attached to a rotary drill 100. Preferably, the ruler 94, the fixation pin 96 and the driver 98 are all made of stainless steel, or other metal, although other materials are also contemplated.

Briefly, in order to mark the location of the provisional, the ruler 94 is attached to the fin clamp's arm 64, and the fixation pin 96 is temporarily driven into the humerus 18 at a position within the ruler's slot 95, and the position of the pin with respect to the ruler is noted. Then, the provisional 22, the fin clamp 60 and the ruler 94 are removed, but the fixation pin 96 remains in place in the humerus. The permanent stemmed humeral component is inserted into the humerus, and the fin clamp 60 and ruler 94 are attached thereto, as they were attached to the provisional. The position of the assembly of the permanent stemmed humeral component, the fin clamp and the ruler is adjusted until the fixation pin is positioned at the same spot within the slot on the ruler that was previously noted. Thus, by using the fin clamp, the ruler and the fixation pin (and pin driver)—the version and height of the provisional can be been duplicated for the permanent humeral component.

Figure 10:
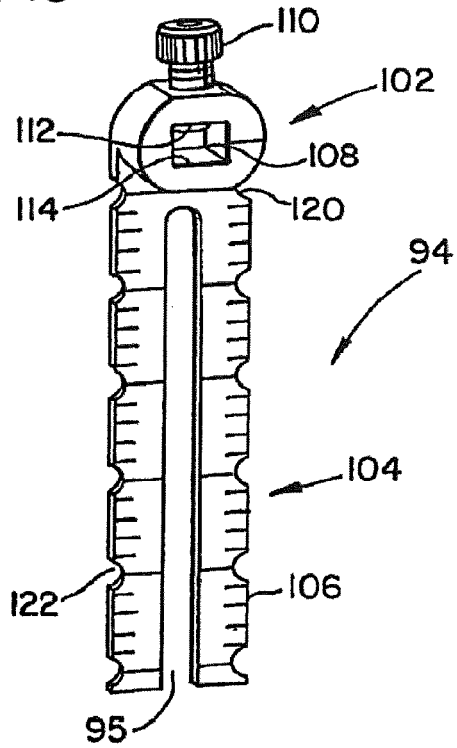
FIG. 10 is a perspective view of the ruler of FIG. 9.

Details of the preferred embodiment of the ruler 94, the fixation pin 96 and the pin driver 98 will be described next, while making reference to FIGS. 9-13. FIG. 10 shows a perspective view of the preferred embodiment of the ruler 94, which includes a securing assembly 102 and a main body 104 that has a scale 106 and the slot 95 mentioned above. The securing assembly 102, which is used to secure the ruler 94 to the arm 64 of the fin clamp 60 (as shown in FIG. 9), preferably includes an opening 108, which allows the ruler to be slid upon the arm 64 of the fin clamp 60. Preferably, the opening 108 is large enough to allow the arm 64 to slide through with ease, but not so large that the ruler is free to rotate about the arm. It is also desirable to configure the opening 108 with flat upper and lower surfaces 112, 114, which, in combination with the flat upper and lower surfaces 116, 118 of the fin clamp's arm 64 (FIG. 4), also prevent the ruler 94 from unduly rotating on the arm 64. The securing assembly 102 also includes a setscrew 110 that extends into a threaded hole that goes into opening 108. By tightening the setscrew 110, the ruler 94 can be secured upon the arm 64. Preferably, the setscrew 110 includes a flat bottom, which provides better lateral stability for the ruler when it is attached to the arm. Although only a setscrew-based securing assembly 102 has been shown and described, other mechanisms for securing the ruler to the arm are also contemplated.

As can be seen in FIG. 10, the scale 106 includes a plurality of incremental marks. Although not shown, periodic numerals may also be added for ease of reference. It should be noted that the scale 106 is preferably based on the same scale with the same zero point used for the fin clamp 60, which was shown and described while referring to FIG. 7. Thus, in this preferred embodiment, the upper incremental mark 120 on the ruler 94 would be designated as 15 mm (and not zero) because when the ruler is properly secured upon the arm 64 of the fin clamp 60, the incremental mark 120 is located 15 mm from the zero point on the humeral stem provisional (or the stemmed humeral component). Optionally, a series of peripheral grooves 122 may also be provided on each side of the main body 104 at regular increments (such as every 10 mm) in order to facilitate reading the scale.

Figure 11:
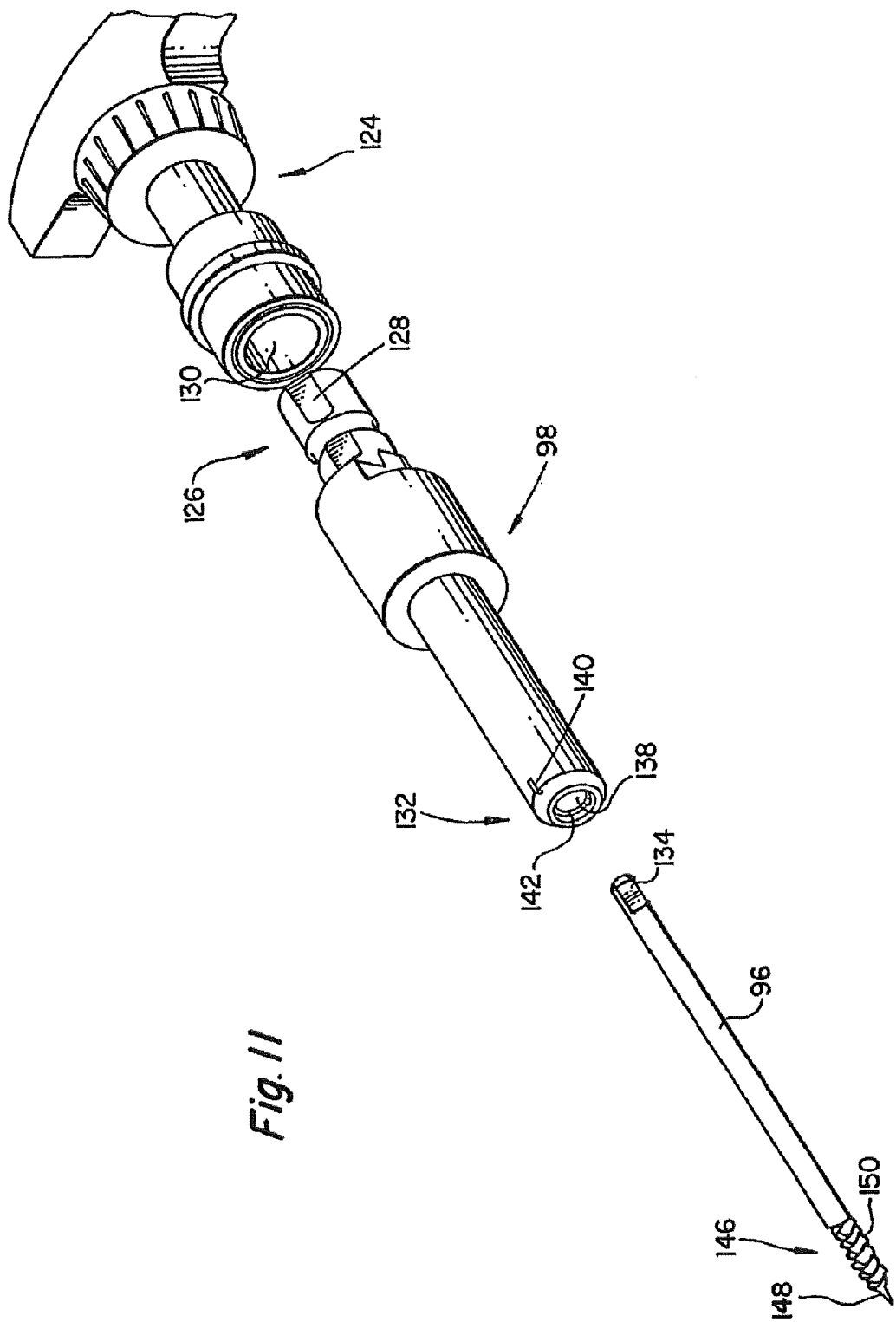
FIG. 11 is a perspective view of the fixation pin and driver of FIG. 9, except instead of including a portion of the drill, this figure includes a T-handle.

FIG. 11 shows an example of the preferred embodiment of the pin 96 and the pin driver 98, as well as a T-handle 124 that can be attached to the pin driver for manually rotating the pin. If desired, the T-handle 124 can be used in place of the rotary drill 100 mentioned earlier, if manual insertion of the pin is desired. The end of the pin driver 98 is preferably configured to accept either the T-handle 24 or the drill 100. In order to transfer rotation from the T-handle 124 or the drill 100 to the pin driver 98, one end 126 of the driver preferably includes one or more flat surfaces 128, and forms the male portion of a male/female connection, where the female portion is found on end 130 of the T-handle 124 (of the drill 10), the interior periphery of which is shaped to correspond to end 126 of the pin driver 98, and included the same number of flat surfaces as found on the driver. In the preferred embodiment, there are three flat surfaces 128 on the male portion formed on the driver. Accordingly, there would also be three flat surfaces on the female portion formed on the T-handle or drill. Of course, cross-sectional shapes other than those described can also be used to transfer rotation from the T-handle (or drill) to the pin driver 98.

Figure 13:
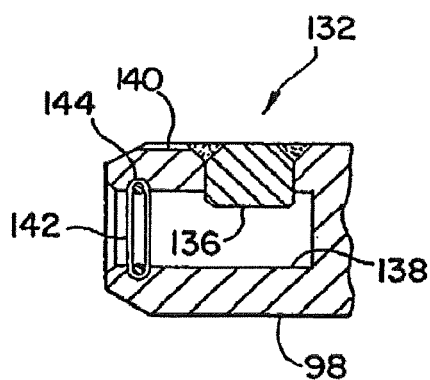
FIG. 13 is cut-away view of the end of the driver into which the fixation pin is inserted.

The other end of the driver 98, end 132, should also include means for transferring rotary motion, but this time the rotary motion is being transferred from the pin driver 98 to the pin 96. Accordingly, the pin driver and the pin should include mating male/female portions of corresponding non-circular cross-sections. In the preferred embodiment shown in FIG. 11, a flat portion 134 is used to create a non-circular cross-section on the pin 96, which defines the male portion of the connection. As best shown in FIG. 13, a corresponding flat portion 136 is created on the inner periphery of end 132 of the driver 98, thereby creating a female portion with a corresponding non-circular cross-section. Although only one type of non-circular cross-sectional shape is being shown and described, other non-circular cross-sectional shapes may also be used, as long as they allow the transfer of rotary motion between the driver and the pin.

For ease of manufacture, the flat portion 136 of the driver 98 may be formed during a separate process after aperture 138 has been drilled. In the preferred embodiment, flat portion 136 is formed by depositing material, such as the same metal used for driver 98, into a cavity 140 formed near end 132 of the driver. In order to catch and shape the material, a mold is inserted into aperture 138 to create the desired shape of the flat portion 136. Once the material placed into cavity 140 has dried, the mold is removed and the outer periphery can be machined to create a smooth outer periphery. Drilling a circular aperture 138 and inserting a plug of material in a cavity 140 is easier, and less costly, than directly attempting to machine an aperture with a flat surface.

To inform the surgeon of the location of the flat surface 136 on the driver 98 so that the flat surface 134 of the pin can be properly oriented to contact the flat surface 136 when the pin is inserted into the driver, a line 140 or other type of mark may be engraved or otherwise made on the outer periphery of end 132 of the driver 98. In order to more tightly secure the pin 96 within the driver 98, a C-ring 142 is preferably seated within a channel 144, as shown in FIG. 13. The channel 144 is preferably formed in an area of the aperture 138, of circular cross-section, that is between the location of the flat surface 134 and end 132.

Figure 12A:
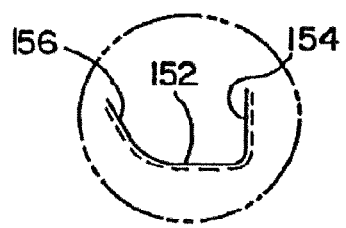
FIG. 12A is an enlarged view taken within circle 12A of FIG. 12.
Figure 12:
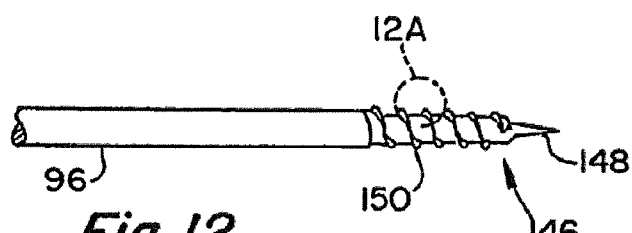
FIG. 12 is a view of the end of the fixation pin, with an enlarged view of one of the screw threads.

Turning now to FIGS. 11, 12, and 12A, the pointed end 146 of the pin 96 will be discussed. As mentioned earlier, the pin 196 is temporarily inserted into the humerus after the humeral stem provisional has been properly positioned, in order to facilitate re-creation of that position for the stemmed humeral component. Accordingly, the pointed end 146 of the pin must be configured so that it can be easily inserted/removed to/from the bone, and also so that when it is inserted into the bone, it remains securely in position. The preferred embodiment of the pointed end includes a knife edge tip 148 and a sharpened threaded portion 150.

The knife edge tip 148 is used for cutting the initial pathway for the remainder of end 146 of the pin 96 being inserted into the bone. The knife edge tip 148 is preferably generally flat, and generally triangular-shaped. The two edges that converge to form the tip are preferably sharpened, so that the tip can be easily inserted into the bone when the pin is rotated.

FIG. 12A shows a magnified section of the sharpened threaded portion 150, taken from within circle 12A of FIG. 12, which shows a trough 152 between two sections of the thread in order to illustrate the preferred configuration of the threaded portion. More specifically, FIG. 12A shows how a trailing edge portion 154 of the thread continues into a trough 152 and how it further continues into the leading edge portion 156 of the next section of thread. As shown in the figure, the leading edge portions 156 are sloped, preferably at approximately 35 degrees, to facilitate cutting into the bone. In contrast, the trailing edge portions 154 are essentially normal to the axis of the pin 96 (or they may be slightly sloped at approximately 3 degrees), which helps to prevent the pin from becoming dislodged from the bone.

To provide for better understanding of the present invention, the method of using the tools described above will be summarized, without the detailed descriptions of the tools themselves already provided, while referring primarily to FIGS. 2, 8 and 9. After the humeral canal has been prepared and the proper size of stemmed humeral component has been selected, a humeral stem provisional 22 of the same size as the humeral component is selected, an appropriately sized sleeve 25 is attached to the provisional's stem 24, and the desired fin clamp is attached to the provisional. The provisional 22 (with a fin clamp and a sleeve attached) is inserted into the humeral canal, and the selected fin clamp (60, 60' or 60") is used to properly position the provisional within the humeral canal. Although the appropriate fin clamp is preferably attached to the provisional prior to its insertion into the canal, the fin clamp may also be attached to the provisional after insertion into the canal, if desired. Attachment of the fin clamp to the provisional is accomplished by tightening the setscrew located on the proximal side (72 or 74; 72' or 74'; 72" or 74"). The appropriate fin clamp is selected depending upon whether the operation relates to the left shoulder or the right shoulder, and whether the desired separation distance between the proximal end of the humerus 38 and the distal side 36 of the collar 26 is intended to be 15 mm, 18 mm or 21 mm. Once the appropriate fin clamp (60, 60' or 60") has been selected, the channel 66 is seated on the anterior fin 3 of the provisional 22, as shown in FIG. 8.

After the provisional (with fin clamp and sleeve attached) has been inserted into the humeral canal, it is rotated so that the fin clamp's arm 64 is either aligned with, or slightly posterior of, the bicipital groove 92 (FIG. 1). The axial position of the provisional 22 is adjusted by maintaining the appropriate angled surface (76 or 78; 76' or 78'; 76" or 78") flush with the distal side 36 of the collar 26, while the appropriate flat surface (82 or 80; 82' or 80'; 82" or 80") is made to be approximately flush with the proximal surface 38 of the humeral shaft.

In order to estimate the proper retroversion of the provisional, version pins 84 and 86 (FIG. 8) are inserted into version pin holes 88 and 90, and the patient's arm is extended so that the forearm sits between the version pins. A range of motion analysis is performed. Any necessary adjustments to the location of the provisional are then made. The version pins 84 and 86 are then removed from the version pin holes 88 and 90, and the ruler 94 is attached to the arm 64 of the fin clamp, as shown in FIG. 9, by tightening the setscrew 110.

To mark the position of the provisional 22 before it is removed from the humeral canal, pin 96 is driven into the bone by being rotated, either manually or with a drill, in a location within the slot 95 of the ruler. The position of the pin within the slot is noted so that it can be recreated when the stemmed humeral component is being positioned.

Next, the humeral stem provisional 22, along with the fin clamp and ruler, are removed. The open-ended slot 95 on the ruler 94 permits the ruler to be lifted from the area without disturbing the location of the pin 96. The stemmed humeral component 10 is then inserted into the humeral canal in the position that the provisional previously occupied. The fin clamp is attached to the humeral stem component, and the axial location and retroversion are confirmed by inserting the version pins 84 and 86 and by making any necessary adjustments so that the forearm is between the pins. As an additional check on the position of the humeral component, the ruler 94 is attached to the fin clamp's arm 64, and the position of the alignment pin 96 with respect to the ruler is compared to the position noted earlier. Any necessary adjustments are made. Once the proper position of the stemmed humeral component has been obtained, it is cemented into place in the conventional manner, and the bone fragments are refitted using any one of the desired conventional techniques. The operation is then continued to completion using any desired technique.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method of positioning a stemmed humeral component within a humerus during shoulder arthroplasty, said method comprising the steps of:
    attaching a fin clamp to the stemmed humeral component, the stemmed humeral component comprising a stem and a collar, the collar forming an oblique angle relative to the stem, wherein the fin clamp is attached to the stemmed humeral component such that an angled surface of the fin clamp is contacting and lies flush against a distal side of the collar of the stemmed humeral component;

inserting the stemmed humeral component into a humeral canal at an estimated position; and seating the humeral component at an intended position such that a distal side of the fin clamp is contacting a proximal end of the humerus, which causes the collar of the humeral component to be seated at a certain predetermined distance from the proximal end of the humerus.

2. The method according to claim 1, wherein the fin clamp is attached to the stemmed humeral component after inserting the stemmed humeral component into the humeral canal.

3. The method according to claim 1, wherein said attaching step, said inserting step, and said seating step are each performed twice, once for a humeral stem provisional and once for the stemmed humeral component.

4. The method according to claim 3, further comprising the step of attaching a sleeve upon the stem of the humeral stem provisional prior to said inserting step, wherein said sleeve helps to secure the humeral stem provisional in position within the humeral canal.

5. The method according to claim 1, wherein during said step of inserting the stemmed humeral component at an estimated position, the approximate position of the bicipital groove of the humerus, if intact, is used as a reference for aligning an arm of the fin clamp.

6. The method according to claim 1, further comprising the step of inserting version pins into designated holes in the fin clamp for establishing retroversion of the stemmed humeral component.

7. The method according to claim 1, further comprising the step of performing a range of motion analysis upon the joint with the stemmed humeral component seated within the humeral canal and fin clamp attached to the stemmed humeral component.

8. The method according to claim 1, further comprising the step of attaching a ruler to the fin clamp, while the fin clamp is attached to the stemmed humeral component, for determining an axial position of the humeral component.

9. The method according to claim 8, further comprising the following steps, which are performed prior to said steps of attaching the fin clamp, attaching the ruler to the fin clamp, inserting and seating the stemmed humeral component:

attaching the fin clamp to a humeral stem provisional, the humeral stem provisional comprising a stem and a collar, the collar forming an oblique angle relative to the stem, wherein the fin clamp is attached to the humeral stem provisional such that an angled surface of the fin clamp is contacting and lies flush against a distal side of the collar of the humeral stem provisional;

inserting the humeral stem provisional into the humeral canal at an estimated position;

seating the humeral stem provisional at the intended position such that a distal side of the fin clamp is contacting the proximal end of the humerus, which causes the collar of the humeral stem provisional to be seated at a certain predetermined distance from the proximal end of the humerus;

attaching a ruler to the fin clamp, while the fin clamp is attached to the humeral stem provisional, for determining the position of the humeral stem provisional;

inserting at least one fixation pin into the humerus at a point near the ruler, in order to facilitate proper positioning of the stemmed humeral component into the same location as the humeral stem provisional; and removing the humeral stem provisional, with the ruler attached thereto, while maintaining the at least one fixation pin inserted into the humerus.

10. A method for temporarily securing a humeral stem provisional within a humerus during shoulder arthroplasty, said method comprising the steps of:

attaching a sleeve to a stem of the humeral stem provisional, the stemmed humeral component comprising a collar that forms an oblique angle relative to the stem;

inserting the humeral stem provisional, with the sleeve attached thereto, into a canal located within a proximal portion of the humerus;

attaching a fin clamp to the humeral stem provisional such that an angled surface of the fin clamp is contacting and lies flush against a distal side of the collar of the humeral stem provisional;

seating the humeral stem provisional at an intended position such that a distal side of the fin clamp is contacting a proximal end of the humerus;

after determining that the humeral stem provisional is properly sized and positioned, removing the humeral stem provisional and the sleeve; and implanting a permanent humeral component in the same location and orientation as the humeral stem provisional previously removed.

11. The method according to claim 10, further comprising the step of selecting a sleeve of an appropriate size to correspond to the size of the humeral stem provisional being used.

12. The method according to claim 11 wherein a sleeve of a single size corresponds to a plurality of humeral stem provisionals of a plurality of different sizes.

* * * * *